United States Patent
Trimbo et al.

(12) 
(10) Patent No.: US 6,306,828 B1
(45) Date of Patent: Oct. 23, 2001

(54) ENANTIOMERICALLY-ENHANCED NUTRITIONAL ENERGY SUBSTRATES

(75) Inventors: Susan Trimbo, Evanston, IL (US); Xavier Leverve, Grenoble (FR); Bruce Rowe, Evanston, IL (US); Francis Rosé, Paris (FR); David Eugene Pereira, Crystal Lake; Patrick Francis Jonas, Waukegan, both of IL (US)

(73) Assignee: Baxter International, Inc., Deerfield, IL (US)

( * ) Notice: Subject to any disclaimer, the term of this patent is extended or adjusted under 35 U.S.C. 154(b) by 0 days.

(21) Appl. No.: 08/417,943

(22) Filed: Apr. 6, 1995

(51) Int. Cl.$^7$ ..................................................... A61K 31/70
(52) U.S. Cl. .............................. 514/25; 514/23; 536/115; 536/119
(58) Field of Search .................................. 536/115, 119; 514/23, 25

(56) References Cited

U.S. PATENT DOCUMENTS

| | | | |
|---|---|---|---|
| 4,665,057 | 5/1987 | Nelson et al. | 514/23 |
| 4,701,443 | 10/1987 | Nelson et al. | 514/23 |
| 5,256,697 | 10/1993 | Miller et al. | 514/625 |
| 5,263,260 | 11/1993 | Smith | 33/526 |
| 5,264,237 | 11/1993 | Traitler et al. | 426/611 |
| 5,283,260 | 2/1994 | Miller et al. | 514/563 |
| 5,308,832 | 5/1994 | Garleb et al. | 514/2 |

FOREIGN PATENT DOCUMENTS

SHO 53-34712  3/1978 (JP).
SHO 53-34713  3/1978 (JP).

OTHER PUBLICATIONS

Guignier, "Role du lactate dans le metabolisme intermediaire interet en reanimation", Conf. XIX Congres de la Societe de Reanimation de Langue, Francaise, Paris, Nov. 22–25, 1990.

Maran, et al., "Protection by lactate of cerebral function during hypoglycaemia", *The Lancet*, vol. 343, Jan. 1, 1994.

Halperin, et al., "Ketoacidosis and Lactic Acidosis", *Diabetes/Metabolism Reviews*, vol. 5, No. 4, Jun. 1989.

Jensen, et al., "Effect of Lactate, Pyruvate, and pH on Secretion of Angiogenesis and Mitogenesis Factors by Macrophages", *Laboratory Investigation*, vol. 54, No. 5, p. 574, 1986.

Hermansen, et al., "Production and Removal of Lactate during Exercise in Man", Acta Physiol. Scand., 1972, 86, 191–201.

Amiel, "Nutrition of the brain: macronutrient supply", Symposium on "Nutrition of the Brain", Proceedings of the Nutrition Society, Winter Meeting of the Nutrition Society, London, Jan. 27, 1994.

Feldmann, et al., "Esters of DL–Lactic Acid with Glycerol and Fructose", *Arch Biochem*, vol. 14, pp. 117–124, 1947.

*Primary Examiner*—Elli Peselev
(74) *Attorney, Agent, or Firm*—Jeffrey C. Nichols; Mark J. Buonaiuto; Francis C. Kowalik

(57) ABSTRACT

Synthetic enantiomeric esters are employed as energy substrates for parenteral or enteral nutritional formulations. The substrates are provided in substantially monoisomeric or anomeric forms readily utilized in patient metabolism.

7 Claims, No Drawings

ENANTIOMERICALLY-ENHANCED NUTRITIONAL ENERGY SUBSTRATES

BACKGROUND OF THE INVENTION

The present invention generally relates to the field of enteral and parenteral nutritional formulations. More particularly, it relates to new and improved enantiomerically-enriched energy substrates for use in nutritional formulations providing high caloric density and low osmolarity which may also be used to beneficially direct intermediate metabolism in metabolically impaired patients.

Nutritional formulations are known which are used to supply the total nutritional needs of a patient. Other nutritional formulations are intended as supplements to provide certain special nutritional needs associated with various patient conditions and/or disease states. Most formulations include a protein component, a carbohydrate component and a lipid component.

The energetic and protein needs of patients having high metabolic activity are difficult to satisfy. Fats or lipids represent the richest nutrients from the point of view of energy. However, excessive consumption of fats presents a large number of health risks, especially cardiovascular health risks. Certain metabolic disorders involving lipids such as hyperlipidemia, obesity and diabetes also require restricted intake of fats generally, and saturated fats and cholesterol, in particular. The use of various substrates in nutritional formulations in above-normal quantities may induce metabolic perturbations and imbalances in the homeostasis of the patient.

It has been determined that not only the quantity but also the component makeup of the lipid fraction of a nutritional formulation may be very important for patients suffering from certain disease states or recovering from surgery, chemotherapy or traumatic injury. For example, hypernutrition for patients with respiratory failure may be a problem. Long chain triglycerides (LCTS) should be avoided during sepsis. Patients with insulin resistance should have their glucose requirements carefully regulated. The formulations, depending on their chemical composition, may also cause intestinal transit problems leading to diarrhea.

U.S. Pat. No. 5,283,260 to Miller, et al., describes the use of pyruvyl amino acid compounds, as alternative energy sources for the treatment of obesity and diabetes.

U.S. Pat. No. 5,283,260 to Galeb, et al., describe the use of low glucose-containing nutritional formulations for head trauma patients based on n-6 and n-3 fatty acids as alternative energy sources.

Hermanson, et al. in *Acta Physiol. Scand.*, 1972, Vol. 86, pages 191–201, disclosed their findings that blood lactate appears to be metabolized by skeletal muscle in significant quantities rather than exclusively by the liver as was previously thought.

Jensen, et al., in *Laboratory Investigation*, Vol. 54, No. 5, page 574, 1986, describe a study which indicated that high lactate concentration encouraged macrophage cultures to secrete angiogenesis factors. Jensen, et al. concluded that high lactate concentrations may stimulate angiogenesis in wound healing. The authors also found that pyruvate did not cause the same response.

Stephanie Amiel, in *Proceedings of the Nutrition Society*, (1994), Vol. 54, pages 401–405, states that lactate studies suggest that lactate is able to support cerebral glucose metabolism and maintain cognitive functions during hypoglycemia. The author states that the development of therapeutic regimens to provide non-glucose fuels for cerebral metabolism during hypoglycemia needs to be more fully explored.

Maran, et al. in *The Lancet*, Vol. 343, Jan. 1, 1994, describe lactate as protective of brain function during hypoglycemia and recommend its therapeutic use in treating insulin dependent diabetes mellitus patients.

Some lipid components may be metabolized to form substrates whose concentration positively or negatively may affect the equilibria of other substrates. Moreover, many substrates may only be metabolized if present in a specific isomer form, such as (S)-(−) lactate, D-glucosides and the like. The presence of unhelpful and unusable substrates in nutritional formulations may lead to various problems including incomplete metabolism, toxic metabolites, side effects, and insufficient water solubility, to name but a few. It has been suggested that providing lactate may shift the equilibrium of the LDH enzyme catalyzed reaction:

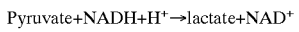

$$\text{Pyruvate} + \text{NADH} + \text{H}^+ \rightarrow \text{lactate} + \text{NAD}^+$$

to the left, preventing or reducing the likelihood for developing lactic acidosis. Nutritional formulations having lipid fractions which comprise substantially only the useful enantiomeric forms of certain substrates and metabolites are generally not known.

SUMMARY OF THE INVENTION

The present invention provides new and improved enantiomerically-enhanced energy substrates for use in nutritional formulations.

In an embodiment, new energy substrates comprise monoisomeric forms of glyceryl tri(chiral alkanoates). An example of an energy substrate of this type includes a synthetic triester of glycerol with (S)-(−)-lactic acid, providing three enantiomerically appropriate, so-called "L-form" lactate moieties per glycerol molecule.

In an embodiment, a method for making substantially monoisomeric chiral alkanoic acid esters is provided in which a protected chiral intermediate is formed before esterification and, after esterification is complete, the chiral protecting group is removed to yield the chiral ester product. Asymmetry of all asymmetric carbons is maintained through the reaction process without forming undesirable isomeric or other byproducts or intermediates.

In accordance with still another embodiment, enantiomerically enhanced nutritional substrates comprising anomeric glucoside and galactoside-containing alkanoic acid esters are provided. An example of these substrates includes an anomeric mixture of α,β-D-glucopyranosyl $C_2$–$C_{20}$ alkanoate, wherein the ratio of α:β anomers is greater than about 2:1, respectively. A synthetic method for directly making these substrate compositions employing protected chiral intermediates is also provided by this invention.

In a further embodiment, novel enantiomerically enhanced nutritional substrates comprising chiral α- or β-hydroxyalkanoyl $C_2$–$C_2$ alkanoic acid esters and methods for making them are provided.

In another embodiment of the invention, new and improved nutritional formulations are provided comprising an enantiomerically enriched lipid fraction designed to provide high caloric density and low osmolarity. The new lipid fraction comprises at least one enantiomerically enriched energy substrate selected from chiral α- and/or β-hydroxyalkanoyl alkanoates, glyceryl tri(chiral alkanoates), anomeric α,β-D-glycopyranosyl alkanoates and mixtures of any of these substrates.

In accordance with a further embodiment of the invention, a method for treating a patient previously diagnosed as having a metabolic disorder or suffering from trauma or nutritional deficit is provided comprising administering to the patient an improved nutritional formulation including an enantiomerically-enhanced lipid fraction.

An advantage of the present invention is that new substrates and formulations are provided for enteral and parenteral nutrition which are present in biologically available forms.

Another advantage provided by the present invention is that new and improved substrates, lipid fractions and nutritional formulations are provided which are adapted to be used in enteral and parenteral nutritional formulations. The formulations are intended for therapeutic use in treating various metabolic disorders, post-operative, traumatic and/or disease conditions of a patient.

In accordance with the present invention, new energy substrates are provided having good caloric density. For example, in an embodiment, a preferred substrate comprises glucose octanoate. The molecular weight of glucose octanoate is 306 g/mole. ATP yield per mole of glucose=30 moles of ATP per mole of glucose oxidized to $CO_2$ and $H_2O$. ATP yield per mole of octanoic acid=48 moles of ATP per mole of octanoic acid oxidized to $CO_2$ and $H_2O$. Total ATP yield per mole of glucose octanoate=78 moles of ATP per mole of glucose octanoate oxidized to $CO_2$ and $H_2O$. Using the generally accepted energy yield for the hydrolysis of the terminal phosphate of ATP of 23 kcal/mole, the energy density of glucose octanote is 1794 kcal/mole. The energy density of glucose octanoate per gram is 5.86 kcal/gram.

In another embodiment, the energy substrate is glyceryl octanoate. The caloric density of glyceryl octanoate may also be calculated. The molecular weight of glyceryl octonoate=236 g/mole. ATP yield per mole of glycerol=16 moles of ATP per mole of glycerol oxidized to $CO_2$ and $H_2O$. ATP yield per mole of octanoic acid=48 moles of ATP per mole of octanoic acid oxidized to $CO_2$ and $H_2O$. Total ATP yield per mole of glyceryl octanoate=64 moles of ATP per mole of glyceryl octanoate oxidized to $CO_2$ and $H_2O$. Using the generally accepted energy yield for the hydrolysis of the terminal phosphate of ATP of 23 kcal/mole, the energy density of glyceryl octanote is 1472 kcal/mole. The energy density of glyceryl octanoate per gram is 6.24 kcal/gram.

In another embodiment, a preferred energy substrate is glyceryl trilactate. The caloric density of glyceryl trilactate may also be calculated. The molecular weight of glyceryl trilactate=308.33 g/mole. ATP yield per mole of lactate=19 moles of ATP per mole of lactate oxidized to $CO_2$ and $H_2O$. ATP yield per mole of glycerol=16 moles of ATP per mole of glycerol oxidized to $CO_2$ and $H_2O$. Total ATP yield per mole of glyceryl trilactate=73 moles of ATP per mole of glyceryl trilactate oxidized to $CO_2$ and $H_2O$. Using the generally accepted energy yield for the hydrolysis of the terminal phosphate of ATP of 23 kcal/mole, the energy density of glyceryl trilactate is 1679 kcal/mole. The energy density of glyceryl trilactate per gram is 5.45 kcal/gram. The comparable values for glucose are 690 kcal/mole and 3.8 kcal/gram (conventionally rounded up to 4 kcal/gram).

The new and improved energy substrates in accordance with the invention may be administered parenterally, enterally, intraperitoneally or topically. The substrates may be given alone or in combination with other nutrients, drug carriers or diluents.

The new and improved energy substrates provided by the present invention may be utilized by a number of tissues under a variety of physiological or pathological conditions. The new and improved substrates may be administered to a patient suffering from nutritional deficit or depletion such as experienced after prolonged exercise such as marathon running. The substrates and formulations containing them may be administered to patients experiencing poor tissue oxygenation or other forms of ischemia to prevent, or improve the recovery of, organ failure, such as hepatic or renal failure. Another use of the substrates is to promote wound healing after trauma or surgery. The substrates may also be used to successfully control hypoglycemia in diabetic patients, as well as, in patients suffering from obesity. Moreover, the new and improved substrates may also be used for patients suffering from neurological injuries such as head trauma.

Other advantages of this invention will become apparent from the following Detailed Description and Examples.

DETAILED DESCRIPTION OF THE INVENTION

In accordance with this invention, new and improved nutritional formulations for providing improved nutritional therapy for patients incorporate new and improved enantiomerically-enriched or enhanced energy substrates. As used herein, the term enantiomerically-enriched means a substrate provided in a particular stereoisomeric form which is readily utilizable and in which non-useful or less useful stereoisomeric forms of the compound usually present with the desired substrate are absent or present in substantially reduced amounts.

The new and improved enantiomerically-enriched substrates useful for making new and improved enantiomerically-enhanced nutritional formulations generally comprise esters derived from substantially monoisomeric or substantially anomeric chiral group containing alkanoic acids or hydroxyl-group containing compounds. The new and improved chiral ester energy substrates are generally represented by the formula:

(1)

wherein A is a residue of hydroxyl-group containing compound selected from alcohols, diols, triols and polyols, and B is a residue of a $C_2$–$C_{20}$ alkanoic acid, wherein either A, or B, or both A and B include at least one chiral carbon and are present in a biologically useful isomeric form.

In accordance with an embodiment of the invention, compounds useful for contributing or forming residue A of formula (1) may be selected from the group consisting of: chiral hydroxy-group containing alkanoic acids or acid derivatives, glycerol, dihydroxyacetone (DHA), anomeric α, β-D-glucopyranose, α,β-D-galactopyranose, α,β-D-glucofuranose and α,β-D-galactofuranose.

Compounds useful for esterification to form residue B of formula (1) may be selected from the group consisting of: $C_2$–$C_{10}$ α- and/or β-hydroxyalkanoic acids, $C_2$–$C_{20}$ alkanoic acids and ester-forming derivatives thereof.

Illustrative acids useful for forming the B residues in the formula include, for example, mono- and dicarboxylic acids, such as butanoic (butyric, $C_4$), pentanoic, hexanoic (capraic, $C_6$), octanoic (caprylic, $C_8$), decanoic (capric, $C_{10}$), dodecanoic (lauric, $C_{12}$), tetradecanoic (myristic, $C_{14}$), hexadecanoic (palmitic, $C_{16}$) and octadecanoic (stearic, $C_{18}$) and alkanedioic acids such as oxalic, malonic, succinic, glutaric, adipic, maleic, fumaric and the like. Other unsaturated fatty acids including oleic, linoleic and linolenic may also be used.

An embodiment of an enantiomerically-enriched energy substrate in accordance with the present invention is a substantially monoisomeric glyceryl tri(chiral alkanoate). The chiral alkanoate esters are generally derived from α- or β-hydroxyalkanoic acids. These chiral alkanoic acids may include, for example, glycolic, lactic, α-hydroxybutyric, mandelic, malic, tartaric, mesotartaric, glyceric and citric acids.

A preferred substrate within this group includes glyceryl tri((S)-(−)-lactate), i.e., a substrate having the formula:

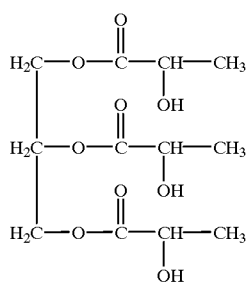

(2)

Another preferred enantiomerically-enriched energy substrate in accordance with the present invention is a substantially monoisomeric chiral α-hydroxyalkanoyl $C_2$–$C_{20}$ alkanoate. Preferred substrates within this group include: (S)-(−)-lactyl alkanoates such as (S)-(−)-lactyl pentanoate and (S)-(−)-lactyl octanoate, e.g., a substrate having the formula:

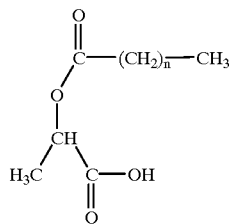

(3)

Another embodiment of an enantiomerically-enriched substrate in accordance with this invention is an anomeric mixture of α,β-D-glucopyranosyl alkanoate, wherein the ratio of a: anomers is greater than about 2:1, respectively, and preferably is about 4:1, respectively. A preferred substrate of this kind includes α,β-D-glucopyranosyl octanoate, generally represented by the formula:

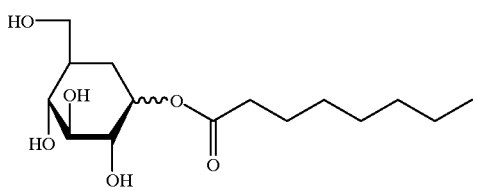

(4)

In accordance with another aspect, the present invention provides a new and improved method for making glyceryl tri(chiral alkanoates). Although glyceryl tri(chiral alkanoate) esters are employed in the following description of the method, other analogous hydroxyl-group containing compounds may be substituted for the glyceryl component, such as dihydroxyacetone, butanediol and the like.

In accordance with the method, a substantially monoisomeric chiral alkanoic acid or acid derivative is first reacted with a chiral protecting reactant to form a protected chiral alkanoic acid intermediate. The protected intermediate is then reacted with a hydroxyl-group containing compound to form a protected alkanoate ester product. Thereafter, the chiral protecting component is removed to yield the substantially monoisomeric chiral alkanoate ester. The chirality or asymmetry of the chiral carbons is maintained in accordance with the method and only desired enantiomerically-enhanced substrates are provided.

In greater detail, the protected alkanoic acid intermediate is first prepared by adding a desired lower alkyl ($C_1$–$C_4$) ester of the desired isomeric form of the chiral α- or β-hydroxy alkanoic acid to a chilled mixture of a strong base in a substantially non-aqueous, polar organic solvent. Thereafter, a chiral protecting group reactant which may be a benzyl halide, such as benzyl bromide, is added and reacted until formation of the protected O-benzyl intermediate is substantially complete. The protected product is separated and purified, for example, by solvent evaporation, followed by ether extraction and distillation of the resulting product.

The protected chiral alkanoate intermediate prepared above, for example, methyl O-benzyl-(s)-lactate, is dissolved in a mixed solvent including water, glacial acetic acid and a strong mineral acid and heated to elevated temperature and thereafter cooled. All solvents are removed by evaporation and the product is separated by extraction into ether to provide a protected chiral alkanoic acid, for example, O-benzyl-(s)-lactic acid.

The protected chiral alkanoic acid intermediate is converted to the corresponding acid chloride by reaction with thionyl chloride in an organic solvent at elevated temperature.

Thereafter, the separated protected chiral alkanoyl chloride is reacted with glycerol in a polar organic solvent at reduced temperature in the presence of an esterification catalyst, e.g., pyridine, to provide the glyceryl tri(protected chiral alkanoate) product, for example, glyceryl tri(O-benzyl-(S)-(−)-lactate), also known as 1,2,3-tri-(O-benzyl-(S)-(−)-lactyl) glycerate).

The protected chiral glyceryl trialkanoate ester is thereafter converted to the desired non-protected glyceryl tri (chiral alkanoate) ester substrate by agitating in an acidic solution in the presence of a reducing catalyst in a reducing atmosphere. The final unprotected chiral triester substrate is thereafter separated and purified to yield the monoisomeric glyceryl tri(chiral alkanoate) product, for example, glyceryl tri(-(S)-(−)-lactate). Similar methods are used for making α,β-D-glucopyranosyl alkanoate substrates, as is more particularly set forth hereinafter in the Examples.

In accordance with another aspect of the invention, new and improved nutritional formulations adapted for general patient nutrition, as well as specialized nutritional therapy, are provided which incorporate one or more of the enantiomerically-enhanced energy substrates of this invention. In accordance with this aspect, the enantiomerically-enhanced energy substrates described herein may be administered to provide metabolic and physiological improvements in the clinical state of the patient.

For enteral and parenteral administration, the selected enantiomerically-enhanced substrate or mixture of substrates is dissolved in a suitable solvent, such as an aqueous solvent, at a desired concentration. This concentration may be that which is intended for use, for example, from about 5 to about 20 mol percent, or it may be more concentrated, for example, from about 10 up to 50 mol percent, or at the saturation solubility limit of the substrate solution. Concentrated solutions are maintained at a greater concentration to enhance the substrate's stability during autoclaving or storage. These solutions may then be diluted to desired administration concentrations at some convenient point before use. If necessary, the enantiomerically-enhanced substrates need not be dissolved in an aqueous solution at all until reconstitution before administration. However, this is not as commercially desirable as supplying ready-to-use forms of solutions.

The enantiomerically-enhanced energy substrate solutions for administration frequently will be mixed with other nutrients or with drugs. Such other nutrients may include nitrogen sources such as amino acids, essential fatty acids such as linoleic or linolenic acid, vitamins, minerals, and electrolytes including trace elements. Other calorie sources such as carbohydrates or other lipids will not ordinarily be needed or may be supplied as required in the clinical context. The amino acids are mixed with the energy substrates prior to or after sterilization.

A mixture of essential amino acids nutritionally balanced according to the Rose proportions would ordinarily be sufficient, although non-essential amino acids may be included. The proportions may be adjusted for special disease states, e.g., inborn errors of metabolism, in accordance with known practice. Supplemental nutrients may also be included to avoid adverse effects on the energy substrates during sterilization and/or storage, for example, accelerated hydrolysis. The pH may range from about 5.5 to about 7.5. other conventional additives, such as antioxidants, buffers or the like, may also be included as desired.

The enantiomerically-enhanced energy substrate containing nutritional solutions may be packaged in conventional parenteral solution containers, either glass or thermoplastic, or in plastic bags. The containers are sterile sealed and will contain some means for communicating with the patient's circulation, either alone or in concert with other devices, hardware or connectors. Typically the means for communicating with the patient's circulation will be a frangible member associated with the container which is adapted to enter into fluid communication with an administration set. The various forms of packaging and administration sets are well known.

The energy substrate solutions may be parenterally administered by infusion into a peripheral vein. The energy substrate concentrations should be selected so that they are not so low as to introduce undue amounts of water into the patient nor so high as to cause peripheral vascular irritation. Generally, an osmolarity below about 600 mOsm is satisfactory for parenteral peripheral infusion. Less advantageously, the solution may be infused through a central venous catheter. The solutions are infused at a rate sufficient to maintain the nutritional status of the patient in concert with the intake of other nutrients. Infusion will ordinarily be from about 25 to 40 kilocalories per kilogram of patient weight per day, but the amount administered parenterally will depend upon the patient's oral intake of energy substrates and other nutrients.

The enantiomerically-enhanced energy substrates herein may also be taken orally and they have the advantage of a higher energy content than glucose so that they are less likely to cause diarrhea or other intestinal problems given at a kilocalorie dose when compared to glucose. The energy substrates, alone or in combination with other nutrients, as described above or with drugs may be taken by gastric tube or as a component of ordinary meals.

Other advantages provided by the present invention will become apparent from the following working

EXAMPLES

Description of the Preferred Embodiments

Example 1

Synthesis of Glyceryl Tri(S)-(-)-lactate)

In accordance with this invention, a preferred chiral alkanoate ester substrate comprises glyceryl tri(s)-(-)-lactate). In accordance with the invention, this new and improved energy substrate may be prepared by a novel method summarized as follows:

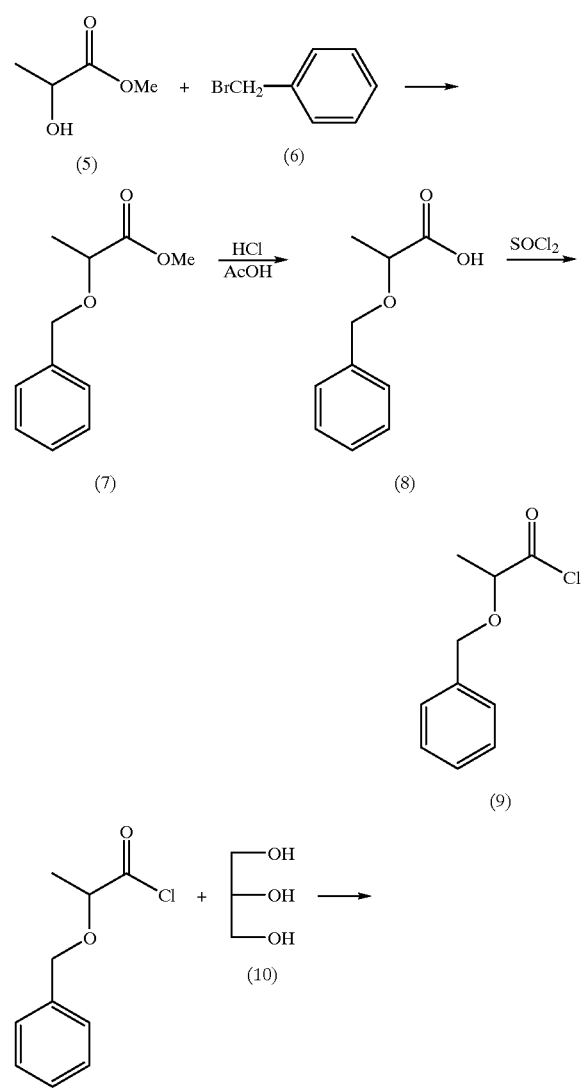

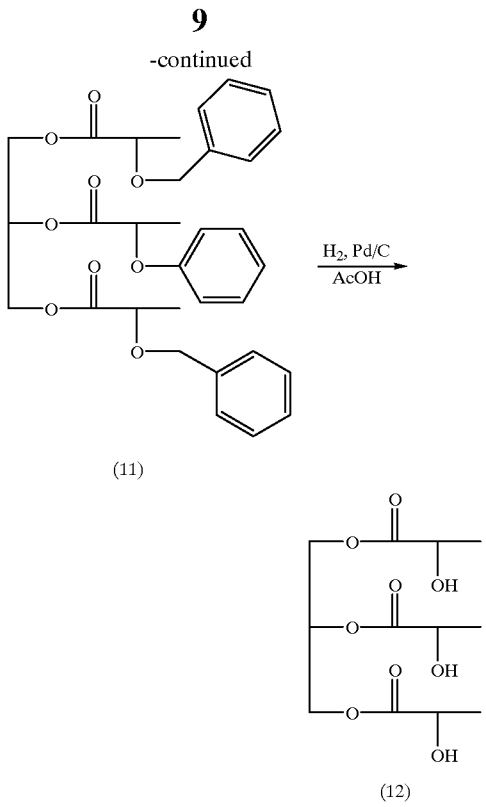

(11)

(12)

Synthesis of Methyl O-benzyl-(S)-lactate (7): A suspension of 95% sodium hydride (23.804 g) in 470 mL of dimethylformamide was cooled in a dry ice/isopropyl alcohol bath to −5° C. To this solution was then added dropwise (S)-(−)-methyl lactate (5), (85 mL) keeping the temperature between −15 and −20° C. After all of the (S)-(−)-methyl lactate had been added the reaction was stirred for one hour. Benzyl bromide (6) (135 mL) was added dropwise and the reaction, after complete addition, was allowed to warm up to room temperature overnight.

The reaction mixture was cooled in an ice bath and 10 mL of distilled water was added dropwise. Most of the dimethylformamide was removed on a rotary evaporator and the residual material was partitioned between diethyl ether and distilled water. The ether layer was separated, washed with water and dried with anhydrous magnesium sulfate. After filtering, the ether was removed on a rotary evaporator and the material was purified by distillation, collecting the material in five fractions with a boiling point range of 78–108° C., at 0.3 to 0.5 mm Hg pressure.

Thin layer chromatography (silica gel, diethyl ether/hexane 2.5:7) showed benzyl bromide to be present in the first two fractions. The other three fractions were combined. H-NMR (CDCl$_3$); 1.44 (d, 3H, —CH$_3$): 3.76 (s, 3H, —O—CH$_3$); 4.08 (q, 1H, —CH); 4.43–4.72 (dd, 2H, benzylic); 7.34 (m, 5H, aromatic) ppm.

Synthesis of 0-benzyl-(S)-lactic acid (8): Methyl O-benzyl-(S)-lactate (7), (36.83 q) was dissolved into a solution of glacial acetic acid (300 mL), distilled water (100 mL) and 5.0 N hydrochloric acid (10.5 mL). The reaction mixture was then heated to 100° C. overnight.

The reaction mixture was cooled to room temperature and most of the solvents were removed on a rotary evaporator. The residual material was partitioned between diethyl ether and distilled water. The ether layer was washed with water, dried with anhydrous magnesium sulfate and filtered. Thin layer chromatography (silica gel, ether/hexane 2.5:7) showed the absence of methyl O-benzyl-(S)-lactate and the appearance of a UV active spot at the origin. The ether was then removed on a rotary evaporator to give 34.17 g of the desired acid. $^1$H-NMR (CDCl$_3$): 1.51 (d, 3H, —CH$_3$): 4.11 (q, 1H, —CH); 4.63 (dd, 2H, benzylic); 7.35 (m, 5H, aromatic); 10.41 (s, 1H, —COOH) ppm.

Synthesis of O-benzyl-(S)-lactyl chloride (9): Thionyl chloride (25 mL) was heated to 80° C. in an oil bath and to this was added dropwise a solution of O-benzyl-(S)-lactic acid (8), (34.17 g) dissolved into 70 mL of toluene. After complete addition, the reaction was stirred at 80° C. for one hour. Most of the solvent was removed at atmospheric pressure and the product was distilled at 100–101° C., at 1.25 mm Hg pressure.

Synthesis of 1,2,3-tri-(O-benzyl-(S)-(−)-lactyl) glycerate (11): A solution of glycerol (10) (1.96 g) in 50 mL of chloroform was cooled in an ice bath and to it was added dropwise O-benzyl-(S)-lactyl chloride (9), (12.92 g). After complete addition of the acid chloride pyridine (6.8 mL) was added dropwise. The reaction was allowed to warm up to room temperature and stirred for one week.

The reaction was diluted with ethyl ether and washed with 1N HCl, distilled water and 5% aqueous sodium bicarbonate. It was then dried with anhydrous magnesium sulfate, filtered and the solvents were removed on a rotary evaporator. The material was further purified using silica gel column chromatography eluting with ethyl ether/hexane (4:9). Purified fractions were pooled and the solvents were removed on a rotary evaporator to give a clear oil. Yield 8.55 g.

Synthesis of tri-(S)-(−)-lactyl glycerate (12): 1,2,3-tri-(O-benzyl-(S)-(−)-lactyl) glycerate (11), (8.55 g) was dissolved into 50 mL of glacial acetic acid and to it was added 1 g of 10% palladium on carbon. The solution was then shaken overnight in an atmosphere of hydrogen with an initial pressure of 50 psi.

The reaction was filtered and purified using silica gel chromatography and ethyl acetate. Purified fractions were combined and the solvent was removed on a rotary evaporator. The clear oil was dissolved into methanol and evaporated on a rotary evaporator. This was repeated two more times. The oil was then dried over phosphorous pentoxide under high vacuum.

$^1$H-NMR (CDCl$_3$): 1.43 (9H, m, —CH$_3$); 2.69 (s, 3H, —OH); 4.40 (m, 5H, —CH$_2$—CH—CH$_2$—); 4.45 (m, 2H, —CH); 5.38 (m, 1H, —CH) ppm.

$^{13}$C-NMR (CDCl$_3$): 20.25, 62.6, 62.8, 66.7, 66.9, 174.8 and 175.1 ppm.

GC-MS as the tri(trimethylsilyl) ether: [M-CH$_3$] ion at m/z 509 indicates a molecular weight of 524 which corresponds to the molecular weight of the tri-protected compound.

An experiment was performed to prove that the synthetic method set forth above did not cause racemiztion, as follows:

Synthesis of methyl (S)-(−)-lactate: Methanol (1 mL) and pyridine (3 mL) were combined into methylene chloride (15 mL). After cooling in an ice bath O-benzyl-(S)-lactyl chloride (3.29 g) was added dropwise. The reaction mixture was then stirred at room temperature for three hours. It was diluted with methylene chloride, washed with 1.00 N HCl, dried with anhydrous magnesium sulfate, filtered and the methylene chloride was removed on a rotary evaporator. The ester had an optical rotation of 55.6° which corresponded to a literature value of 56.1°. Accordingly, no loss of optical purity was detected using this synthetic route.

Example 2

Preparation of Anomeria Mixture of α,β-D-Glucopyranosyl Octanoate

Another preferred enantiomerically-enhanced energy substrate in accordance with this invention comprises α,β-D-glucopyranosyl octanoate. This energy substrate may be prepared in accordance with the method of this invention which is summarized as follows:

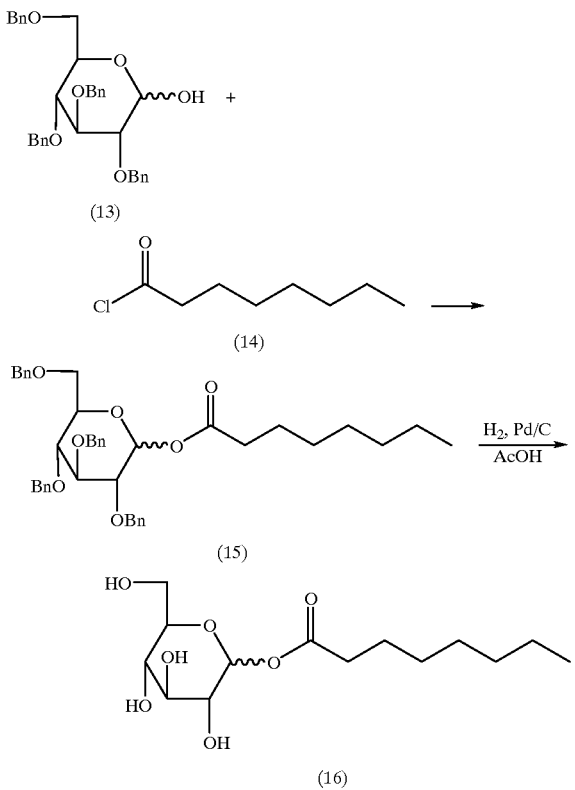

Synthesis of 2,3,4,6-tetra-O-benzyl-α,β-D-glucopyranosyl-octanoate (15): 2,3,4,6-Tetra-O-benzyl-α,β-D-Glucopyranosyl-octanoate (15) was typically prepared in the following manner: 2,3,4,6-Tetra-O-benzyl-α,β-D-glucopyranose (13), (30.0 g, 0.055 mol) and pyridine (30.0 mL) were combined in 140 mL of methylene chloride. Octanoyl chloride (14) (11.4 g) in 60 mL of methylene chloride was added dropwise to the glucose solution at room temperature. The solution was heated at reflux for three hours and then extracted with 1.0 N HCl (3×100 mL), water (1×200 mL) and 5% sodium bicarbonate (3×100 mL). The organic phase was dried ($Na_2SO_4$) and then solvent evaporated to give an oil. The oil was purified by flash column chromatography using silica gel and chloroform:methanol (2000 mL:26 mL) as the eluent. Yield of the ester: 35.9 g (97%). H-NMR and C-NMR spectra were consistent with the structure of the ester.

Synthesis of α,β-D-Glucopyranosyl octanoate (16): Several batches of 1-α,β-D-Glucopyranosyl octanoate (16) were typically prepared in the following manner: 2,3,4,6-tetra-O-benzyl-α,β-D-Glucopyranosyl octanoate (15), (18.1 g, 0.0271 mol) and 10% Pd/carbon (1.742 g) were combined in 250 mL of acetic acid. The mixture was shaken on a Parr Hydrogenator under 60 psi of hydrogen overnight. The mixture was gravity filtered through filter paper. The filter paper was washed with 40 mL of acetic acid, in duplicate. The filtrate was evaporated to an oil. Chloroform (69 mL) was added to the oil and the solution was evaporated to an oil. This was repeated. The oil was purified by flash column chromatography using silica gel (5×40 cm column) and chloroform/methanol (5:2) as the eluent. The fractions containing the product were combined and the solvent evaporated to give an oil. A solid was obtained from ethyl ether. The solids were dried under house vacuum to give 6.51 g of product (78% yield).

$^1$H-NMR ($D_2O$): 0.81 (t, 3); 1.29 (m, 8); 1.60 (m, 2); 2.42 (t, 2); 3.40–3.85 (m, 7); 5.51 and 6.10 (d, 1, α,β anomeric proton) ppm. $^{13}$C-NMR ($D_2O$): 15.1, 23.5, 25.3, 25.4, 30.1, 30.2, 32.3, 34.2, 34.5, 61.0, 61.8, 70.0, 70.2, 71.7, 73.1, 73.5, 75.1, 77.1, 77.9, 83.2, 85.1, 174.3, 174.5 ppm.

The α to β ratio was determined by H-NMR by measuring the integration of the anomeric proton resonances. The α proton resonance is further downfield than the β proton. The ratio of α to β was calculated to be 4:1.

Example 3

Preparation of α-Hydroxyalkanoyl Alkanoate

A chiral alkanoate ester substrate was prepared as follows:

Synthesis of Methyl (S)-3-benzyloxybutyrate (18): Methyl (S)-(+)-3-hydroxybutyrate (17) (2.223 g, 18.82 mmol) and benzyl 2,2,2-trichloroacetimidate (4.2 mL) were dissolved into 37.5 mL of cyclohexane/methylene chloride (2:1). After the addition of 0.2 mL of trifluoromethane sulfonic acid the reaction was stirred under nitrogen for one hour. The reaction was diluted with 75 mL of cyclohexane/methylene chloride (2:1) and filtered. The organic layer was washed with 50 mL of saturated sodium bicarbonate and 50 mL of distilled water. After drying with anhydrous sodium sulfate the solution was filtered and the solvents were removed on a rotovap. The resulting solid was purified using silica gel and elution with ether/hexane (1:4).

Synthesis of (S)-3-benzyloxybutyric acid (19): To a solution of 8.73 g of potassium hydroxide in 140 mL of cold water was dissolved methyl (S)-3-benzyloxybutyrate (18) (24.21 g). The solution was stirred in an ice bath for one hour and at room temperature for one hour. Methanol was added to give a clear solution and the reaction was stirred overnight.

The reaction was concentrated on a rotary evaporator and then extracted with ether. The pH of the aqueous solution was adjusted to 2 with 1N HCl and extracted with ether. The ether solution was dried with magnesium sulfate, filtered and the ether was removed on a rotary evaporator to give 19.27 g of the desired compound (19).

Synthesis of (S)-3-benzyloxybutyrl chloride (20): (S)-3-benzyloxybutyric acid (19) (19.27 g) and thionyl chloride (11 mL) were combined and stirred overnight at room temperature under nitrogen.

Synthesis of glyceryl tris((S)-3-benzyloxybutyrate) (21): A solution of freshly distilled glycerol (2.87 g) in 50 mL of tetrahydrofuran was cooled in an ice bath. To this was then added dropwise (S)-3-benzyloxybutyrl chloride (20) (20.47 g). After complete addition, pyridine (10 mL) was added and the reaction was stirred for four days.

After dilution with ether the reaction was washed with 1N HCl, distilled water and 5% sodium bicarbonate. The solution was dried with magnesium sulfate, filtered and the solvent was removed on a rotary evaporator to give 21.60 g of material. Purification was accomplished with silica gel chromatography eluting first with 1 L of hexane/ether (2:1) and then with hexane/ether 1:1. Purified fractions were combined and the solvents were removed on a rotary evaporator to give 15.40 g of the desired material (21).

Synthesis of glyceryl tris((S)-3-hydroxybutyrate) (22): Glyceryl tris((S)-3-benzyloxybutyrate) (21) (15.40 g) was dissolved into 75 mL of acetic acid and 1 g of palladium on carbon was added. The deprotection was accomplished with an initial pressure of 65 psi of hydrogen. The material was purified by elution through a column of silica gel eluting with ethyl acetate. Purified fractions were combined and the solvent was removed on a rotary evaporator and under high vacuum to give 5.74 g of the desired material (22).

$^1$H-NMR(CDCl$_3$): 5.34 (m, H; 4.38 (m, 2H); 4.22 (m, 4H); 2.64 (s, 3-H); 2.48 (m, 3-H); 2.45 (m, 1); 1.23 (d, 9); $^{13}$C-NMR (CDCl$_3$): 172.4; 172.06; 171.72; 69.17; 64.24; 43.17; 42.93; 42.89; 27.60.

These reactions may be summarized as follows:

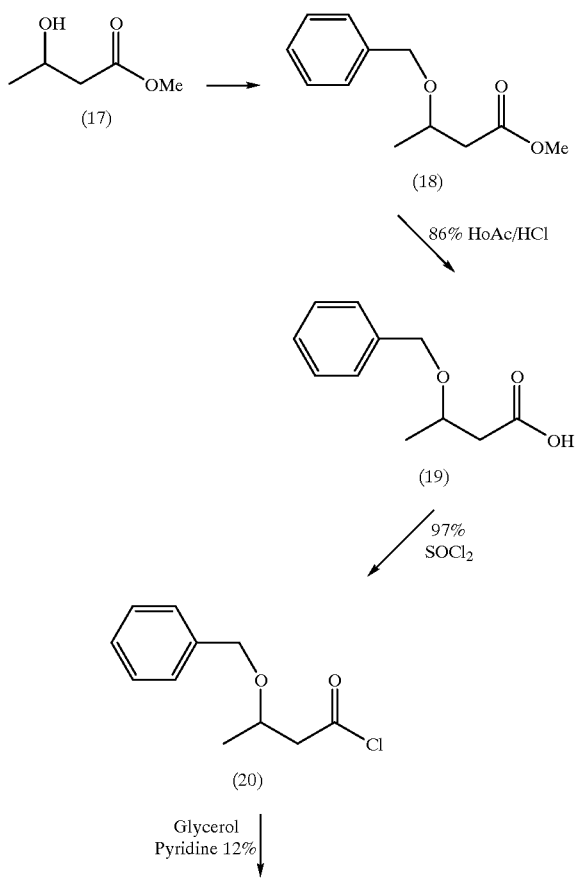

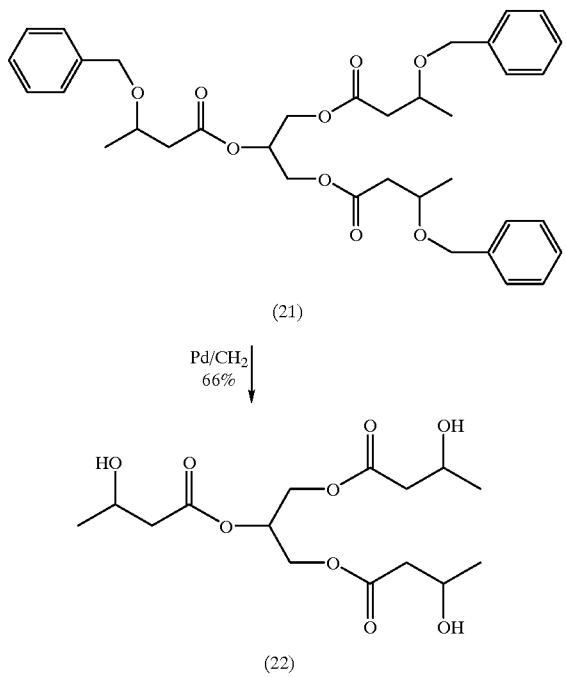

Example 4

Nutritional Formulation Incorporating Enhanced Energy Substrates

A total parenteral nutritional (TPN) formulation incorporating the new and improved enantiomerically-enhanced substrates was prepared in accordance with the Present invention as follows:

| | |
|---|---|
| Amino Acid Mixture | 105 g/Liter |
| Trilactyl Glycerate | 500 mEq/Liter |
| Glucose Octanoate | 800 mEq/Liter |
| Electrolyte Content | |
| NaCl | 30 meq/day |
| NaAcetate | 60 meq/day |
| KCl | 0 meq/day |
| Mg | 16 meq/day |
| Ca Gluc | 10 meq/day |
| Na PO4 | 0 meq/day |
| MVI-12: | 10 mL |
| Vit A | 3300 U |
| Vit B1 | 3 mg |
| Vit B2 | 3.6 mg |
| Vit B5 | 15 mg |
| Vit B6 | 4 mg |
| Vit B12 | 5 mcg |
| Biotin | 60 mcg |
| Vit C | 100 mg |
| Vit D | 200 IU |
| Vit E | 10 IU |
| Folic Acid | 400 mcg |
| Vit K | 0 mg |
| Niacin | 40 mg |
| MTE | 3 ml |
| Chromium | 12 mcg |
| Copper | 12 mcg |
| Iodide | 0 |
| Manganese | 0.3 mg |

-continued

|  |  |
|---|---|
| Molybdenum | 0 |
| Sellenium | 0 |
| Zinc | 4 mg |

This solution provided a total of 2720 Kcal per day (2300 Kcal nonprotein calories). The TPN solution was administered daily over a 20-hour period. The patient received TPN for 9 consecutive days. The pharmacist added vitamins, minerals and electrolytes to the premixed base solution in accordance with the physician prescription. The base solution, which contained amino acids, glucose octanoate and trilactyl glycerate was premixed by the manufacturer in plastic bags and heat sterilized.

Example 5

Assay of Bioavailability and Gross Toxicity of Trilactyl Glycerate in Isolate Rat Hepatocytes In the following experiment, male Wistar rats (200–250 g) fasted for 24 hours were used. Hepatocytes were isolated according to the method of Berry and Friend (1969) as modified by Groen et al. (1982).

The isolated hepatocytes were incubated as follows:

Hepatocytes (final concentration=10 mg dry cell/ml) were incubated in closed vials at 37° C. in a shaking water bath (60 strokes/min) for 30 minutes in 2.5 ml Krebs-bicarbonate buffer (NaCl: 120 mmol/L, KCl: 4.8 mmol/L, $KH_2PO_4$: 1.2 mmol/L, $MgSO_4$: 1.2 mmol/L, $NaCO_3H$: 24 mmol/L, $Ca^{2+}$ :2.4 mmol/L, pH 7.4) containing Bovine Serum Albumin (BSA)-oleate (2%-2 mmol/L), trilactyl glycerate or glucose octanoate (20 mM) The gas atmosphere was $O_2/CO_2$(19:1). After 30 minutes, 0.35 ml samples of the cell suspension were taken and quenched with perchloric acid ($HClO_4$, final concentration 5% (w/v)), then centrifuged at 13,500 g for 5 minutes. The supernatant was neutralized with KOH (2 M) and Mops (0.3 M) for subsequent determination of metabolites. 0.5 ml aliquots of the cell suspension were centrifuged at 13,500 g for 15 seconds. The pellet was frozen in liquid nitrogen and stored at −80° C. to subsequently measure pyruvate kinase activity.

RESULTS

No evidence of gross toxicity, as gauged by hepatocyte viability, was noted. The effects of trilactyl glycerate on the production of various metabolic intermediates are presented in Table 1. These results demonstrate the bioavailability of trilactyl glycerate and its interconversion to glucose. Data on the metabolism of glucose octanoate are given in Table 2. These results demonstrate the bioavailability of the substrate and its utility as a keptone precursor.

TABLE 1

| Metabolite | 0 Mins. | 15 Mins. | 30 Mins. | 45 Mins. | 60 Mins. |
|---|---|---|---|---|---|
| Glucose | 0.006 | 0.027 | 0.062 | 0.178 | 0.189 |
| Pyruvate-Lactate | 0.012 | 0.38 | 0.42 | 0.45 | 0.43 |
| Ketone Bodies | 0.010 | 0.12 | 0.15 | 0.11 | 0.13 |

TABLE 2

| Metabolite | 0 Mins. | 15 Mins. | 30 Mins. | 45 Mins. | 60 Mins. |
|---|---|---|---|---|---|
| Glucose | 0.106 | 0.411 | 0.504 | 0.604 | 0.668 |
| Pyruvate-Lactate | 0.025 | 0.027 | 0.026 | 0.04 | 0.033 |
| Ketone Bodies | 0.023 | 0.101 | 0.161 | 0.200 | 0.257 |

Example 6

Nutritional Therapy for Trauma Patients

A 35-year old male weighing 70 kg is admitted to the emergency room of a trauma center with extensive trauma secondary to an automobile/truck accident. The patient has extensive crushing trauma to the thoracic region, penetrating trauma of the abdomen and fractures of the shoulder and pelvis. Transfusion and fluid and electrolyte therapy were initiated in the emergency room.

A new fluid therapy solution in accordance with the present invention was available to replace Ringer's Lactate Solution. This solution has a more physiological electrolyte profile than Ringer's Lactate which is made possible by adding lactate in an esterified form. The composition of his solution is given below.

| Glycerol Trilactate | 7 mEq/Liter |
|---|---|
| Sodium | 14.0 mEq/Liter |
| Potassium | 4 mEq/Liter |
| Calcium | 3 mEq/Liter |
| Chloride | 147 mEq/Liter |

The patient was admitted to the ICU within 12 hours of hospital admission and was placed on a mechanical ventilator. Initial analysis of the patient's electrolyte status indicated several plasma electrolyte abnormalities and metabolic acidosis with inadequate respiratory compensation. The intravenous fluid replacement solution was changed to a balanced electrolyte solution with bicarbonate precursors (Trilactyl Glycerol and Lactate). The composition of this solution is presented below:

| Glycerol Trilactate | 15 mEq/Liter |
|---|---|
| Sodium | 154 mEq/Liter |
| Potassium | 4 mEq/Liter |
| Calcium | 5 mEq/Liter |
| Magnesium | 3 mEq/Liter |
| Chloride | 146 mEq/Liter |
| Lactate | 20 mEq/Liter |

On the second day following ICU admission of the patient, the diagnosis of adult respiratory distress syndrome (ARDS) with a $PaCO_2/FiO_2$ ratio of less than 200 was made. As part of the therapeutic regimen total parenteral nutrition (TPN) was instituted. The composition of this solution is given below:

| Amino Acid Mixture | 105 g/Liter |
|---|---|
| Trilactyl Glycerate | 500 mEq/Liter |

-continued

| | |
|---|---|
| Glucose Octanoate | 800 mEq/L |
| Electrolytes | As required |
| Vitamins | As required |
| Minerals | As required |

This solution provided a total of 2720 Kcal per day (2300 Kcal nonprotein calories). The TPN solution was administered daily over a 20-hour period. The patient received TPN for 9 consecutive days. The pharmacist added vitamins, minerals and electrolytes to the premixed base solution in accordance with the physician prescription. The base solution, which contained amino acids, glucose octanoate and trilactyl glycerate was premixed by the manufacturer in plastic bags and heat sterilized.

Various clinical and biochemical parameters were monitored to assess the patient's clinical condition; a number of the critical parameters are presented below:

| | Days on TPN | | | |
|---|---|---|---|---|
| | Day 0 | Day 1 | Day 2 | Day 3 |
| $O_2$ Delivery (ml/min) | 812.7 | 886.6 | 1078.4 | 1078.0 |
| $O_2$ Consumption (ml/min) | 211.2 | 193.2 | 256.7 | 317.2 |
| $PaO_2/FiO_2$ | 50.1 | 124.0 | 169.4 | 181.5 |
| Lactate (m/nol/L) | 4.8 | 4.2 | 4.1 | 3.6 |

The patient's condition began to improve by Day 3 of the TPN course. The gradual improvement in $PaO_2$ indicates resolution of the acute respiratory distress syndrome. Lactate concentration was above normal throughout the TPN course; however, values declined gradually suggesting improvement in the patient's course and/or improved lactate clearance. Trilactyl glycerate infusion (as part of TPN) did not induce metabolic acidosis.

Although the present invention has been described with reference to certain preferred embodiments, modifications or changes may be made therein by those skilled in the art without departing from the scope and spirit of the present invention as defined by the appended claims.

We claim:

1. A nutritional composition for providing enteral or parenteral nutrition to a patient comprising:

(a) an α-D-glucopyranosyl $C_2$–$C_{20}$ alkanoate; and (b) a β-D-glucopyranosyl $C_2$–$C_{20}$ alkanoate, wherein the weight ratio of (a):(b) is greater than about 2:1.

2. A nutritional composition as defined in claim 1, further comprising a protein component.

3. A nutritional composition as defined in claim 1, further comprising amino acids.

4. A nutritional composition as defined in claim 1, further comprising vitamins, minerals, electrolytes and trace elements.

5. A nutritional composition as defined in claim 1, further comprising essential fatty acids.

6. A method for providing nutritional support to a patient comprising enterally or parenterally administering to a patient in need of nutritional support a nutritional composition comprising a solution of:

(a) an α-D-glucopyranosyl $C_2$–$C_{20}$ alkanoate; and (b) β-D-glucopyranosyl $C_2$–$C_{20}$ alkanoate, wherein the weight ratio of (a):(b) is greater than about 2:1.

7. A method as defined in claim 6, wherein the patient is in a state of wound healing after surgery or trauma and the nutritional composition is administered to promote wound healing.

* * * * *